(12) United States Patent
Hanley et al.

(10) Patent No.: US 11,019,986 B2
(45) Date of Patent: Jun. 1, 2021

(54) BRONCHOSCOPIC SHEATH FOR MEASURING OR SPACING

(71) Applicant: CSA Medical, Inc., Baltimore, MD (US)

(72) Inventors: Brian M. Hanley, Reading, MA (US); Stephen Griffin, San Jose, CA (US); Heather V. Hawkes, Trumbull, CT (US)

(73) Assignee: CSA Medical, Inc., Lexington, MA (US)

( * ) Notice: Subject to any disclaimer, the term of this patent is extended or adjusted under 35 U.S.C. 154(b) by 116 days.

(21) Appl. No.: 14/848,608

(22) Filed: Sep. 9, 2015

(65) Prior Publication Data

US 2016/0095502 A1    Apr. 7, 2016

Related U.S. Application Data

(60) Provisional application No. 62/047,936, filed on Sep. 9, 2014.

(51) Int. Cl.
| | | |
|---|---|---|
| A61B 1/00 | (2006.01) | |
| A61B 1/267 | (2006.01) | |
| A61B 18/02 | (2006.01) | |
| A61B 90/00 | (2016.01) | |

(52) U.S. Cl.
CPC ...... *A61B 1/00135* (2013.01); *A61B 1/00082* (2013.01); *A61B 1/2676* (2013.01); *A61B 18/02* (2013.01); *A61B 2018/0212* (2013.01); *A61B 2090/0463* (2016.02)

(58) Field of Classification Search
CPC ............ A61B 1/00135; A61B 1/00142; A61B 1/00154; A61B 1/00082; A61B 1/2676; A61B 2090/0463; A61B 18/02; A61B 2018/0212; A61B 1/01; A61B 1/0008
See application file for complete search history.

(56) References Cited

U.S. PATENT DOCUMENTS

| | | | | |
|---|---|---|---|---|
| 5,916,145 A * | 6/1999 | Chu | ............ | A61B 1/00071 600/121 |
| 6,013,047 A * | 1/2000 | King | ............ | A61M 25/0045 604/22 |
| 6,174,280 B1 * | 1/2001 | Oneda | ............ | A61B 1/00078 600/114 |
| 6,199,258 B1 * | 3/2001 | Simon | ............ | G02B 6/4471 29/235 |

(Continued)

*Primary Examiner* — Timothy J Neal
(74) *Attorney, Agent, or Firm* — Kacvinsky Daisak Bluni PLLC

(57) ABSTRACT

A bronchoscopic sheath adapted to be fit over the outside surface of the proximal portion of a bronchoscope to assist with measuring or spacing of treatment. The measurement or spacing sheath is preferably made of braided polymer filament and is configured to collapse under tension and open/expand when the ends of the sheath are pushed towards one-another. Markings are provided on the sheath at regular intervals to reflect distance. The markings may be woven into the braid, or printed on the exterior of the braid. The proximal end of the sheath may be flared and the distal end may be tapered. Each end may be provided with a cuff that may be part of the braid, or a separate elastomeric material, or a thermally sealed edge with atraumatic tip.

20 Claims, 16 Drawing Sheets

(56) References Cited

U.S. PATENT DOCUMENTS

| | | | |
|---|---|---|---|
| 6,575,969 B1* | 6/2003 | Rittman, III | A61B 18/1482 128/898 |
| 2004/0186349 A1* | 9/2004 | Ewers | A61B 1/00082 600/114 |
| 2006/0041270 A1* | 2/2006 | Lenker | A61B 17/3462 606/198 |
| 2006/0287666 A1* | 12/2006 | Saadat | A61M 25/1011 606/198 |
| 2007/0066869 A1* | 3/2007 | Hoffman | A61B 1/00135 600/121 |
| 2007/0123925 A1* | 5/2007 | Benjamin | A61M 25/04 606/194 |
| 2008/0015625 A1* | 1/2008 | Ventura | A61B 17/3439 606/191 |
| 2009/0093675 A1* | 4/2009 | Surti | A61B 1/00135 600/106 |
| 2009/0306471 A1* | 12/2009 | Gettman | A61B 17/3421 600/104 |
| 2009/0318765 A1* | 12/2009 | Torii | A61B 1/00071 600/141 |
| 2011/0023885 A1* | 2/2011 | Vazales | A61B 1/0669 128/207.14 |
| 2013/0030351 A1* | 1/2013 | Belhe | A61F 5/0076 604/9 |

* cited by examiner

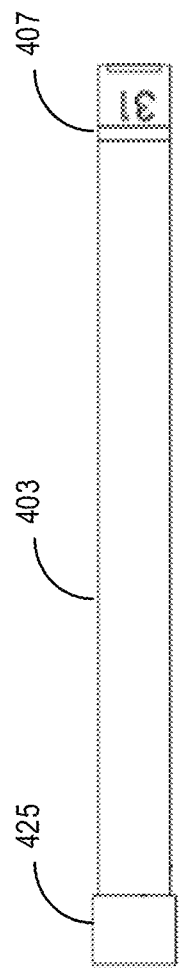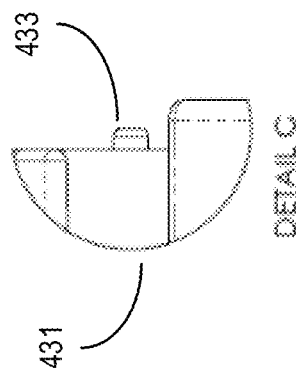
FIG. 8B
FIG. 8C
FIG. 8D

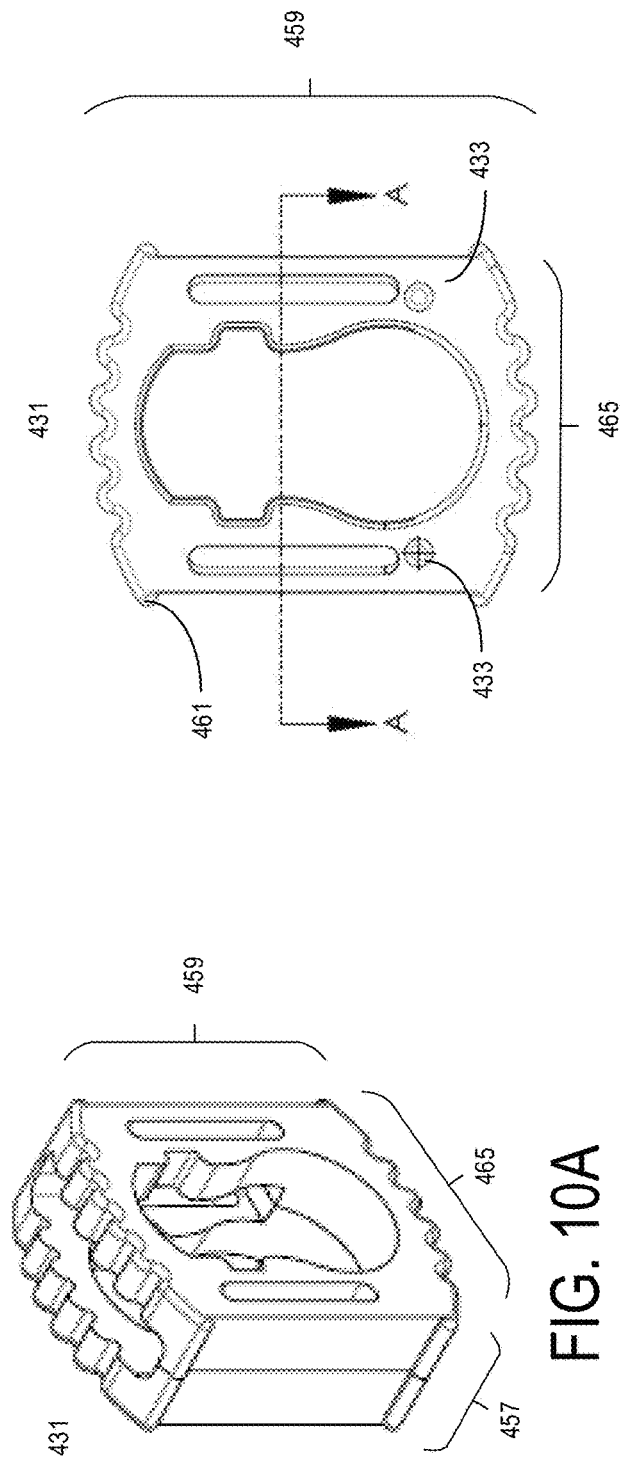
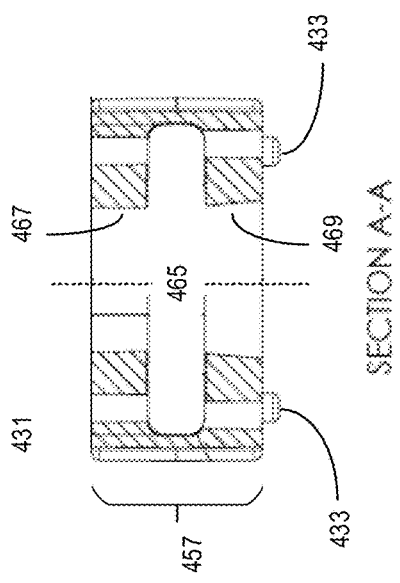
FIG. 10A
FIG. 10B
FIG. 10C

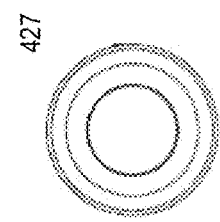
FIG. 11B
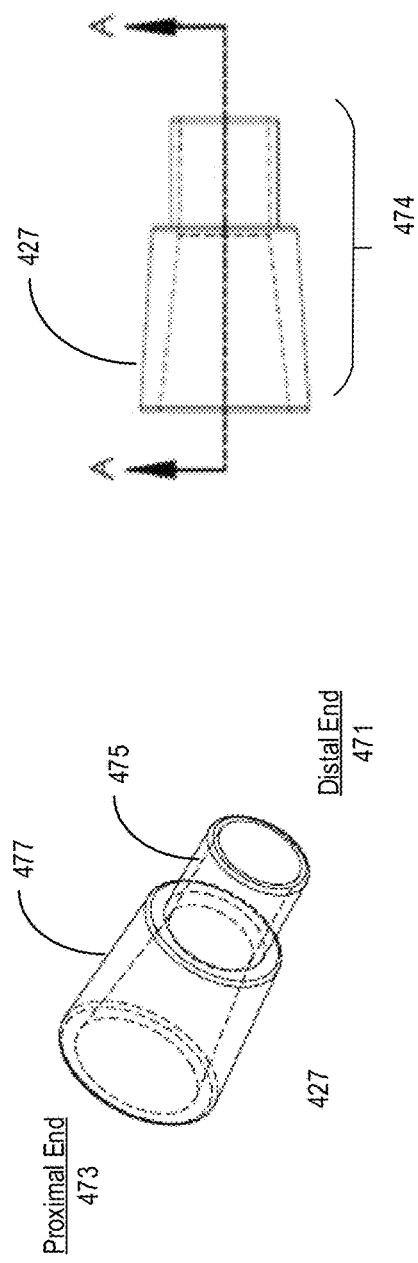
FIG. 11A
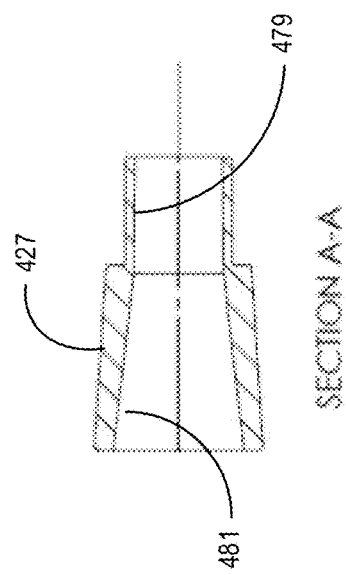
FIG. 11D
FIG. 11C

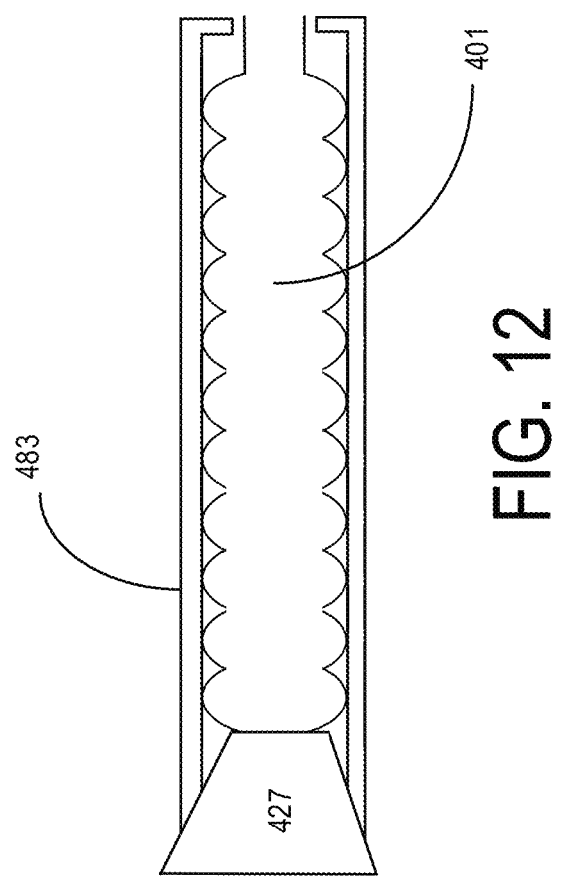

BRONCHOSCOPIC SHEATH FOR MEASURING OR SPACING

RELATED APPLICATIONS

The present application claims priority to U.S. Patent Application Ser. No. 62/047,936, entitled "Bronchoscopic Sheath for Measuring or Spacing" and filed on Sep. 9, 2014. The contents of the aforementioned application are incorporated herein by reference.

FIELD OF THE INVENTION

The invention relates generally to the field of diagnosing, staging and or treating pulmonary diseases utilizing bronchoscopy.

BACKGROUND OF THE INVENTION

Examination and treatment of the airway in humans is generally carried out using a flexible fiber-optic video bronchoscope that is extended into a patient's airway (pharynx, larynx, trachea, bronchi, etc.) through the mouth or nares. Movement of the bronchoscope into and out of the patient's airway is visually monitored by observation of the bronchoscope as it is advanced or withdrawn into the patient and/or by video visualization of the interior of the airway using fiber optics located at the proximal tip of the bronchoscope.

SUMMARY OF THE INVENTION

The present invention is a sheath or sleeve, designed to fit snugly over the outside surface of a bronchoscope during a bronchoscopic procedure. The exterior surface of the sleeve bears markings at pre-determined increments to reflect distance along the length of the sheath which are designed to be used by the practitioner to help gauge and measure movement of the bronchoscope into and out of the patient's airway. The reference markings then are used to reference or align to another object such as the endotracheal tube or rigid bronchoscope.

According to one embodiment, the sheath is made of braided polymer thread/filament. The braid structure is analogous to a Chinese finger puzzle, increasing in diameter when compressed longitudinally, and collapsing/locking down when it is placed under tension. When the sheath is compressed longitudinally, the inner diameter of the sheath expands significantly more than its braided diameter, permitting it to slide over scopes or catheters of a broad range of diameters. When permitted to relax and recover to its original braided dimension, and particularly when it is placed under tension, it fits snugly on the surface of the scope. This allows the sheath to accommodate and provide insulation and reference markings for multiple scope diameters. The braided sleeve Inner Diameter (ID) is intentionally sized smaller than the Outer Diameter (OD) of the preferred bronchoscope such that it expands and fits snuggly to the scope upon insertion. Therefore, the sheath stays tightly fixed to the exterior surface of the flexible bronchoscope during use, but may be easily loaded and unloaded by pushing the ends of the sheath towards one-another, and "inch-worming" the sheath down the length of the bronchoscope shaft.

The reference markings may be printed on the exterior surface of the sheath, e.g., using a pad printer or other method, or may be braided into the sheath, for example using a different colored filament. In either event, the markings are set at defined intervals, e.g., 0.5 cm, 1.0 cm, 1.5 cm, etc. According to an embodiment of the invention, the markings may be made in one color to indicate major lengths, e.g., every 10 cm, and the markings may be made in a different color to indicate minor lengths, e.g., every 1 cm. Whatever markings are used, they may be made according to any known method.

According to an embodiment of the invention, the proximal end of the sheath may be cuffed and/or flared and/or bear a hub to facilitate loading and unloading of the sheath from a flexible bronchoscope. A hub may be a molded or machined plastic component that is joined to the braided sheath by bonding or insert molding.

According to yet another embodiment, the distal end of the sheath may be tapered and or cuffed to facilitate insertion of the sheath-mounted bronchoscope into the sealing gasket of the endotracheal tube, to provide an atraumatic end so that the sheath does not scythe the tissue when moving proximal to distal, and/or to prevent fraying and/or unraveling of the braid.

According to a cuffed embodiment, the cuffs at either end may be thermally formed from the braided material, or they may be formed from a different elastomeric or plastic material and fixed to the end of the braided material according to one of any number of known methods. According to an alternative embodiment, the distal end of the braided sleeve may be dipped in or otherwise coated with a flexible adhesive to create a distal tip that is stiffer to aid with insertion into an endotracheal tube gasket, but still flexible enough to assemble onto the bronchoscope.

According to an embodiment of the invention, the bronchscopic measurement sheath is configured to extend over the flexible bronchoscope a sufficient length to cover the portion of the scope that is visible to the user/operator outside of the patient's body during use, including portions of the scope that are inside the patient's body during part of the treatment but that are withdrawn from the patient's body as progressive parts of the airway tissue are treated. A portion of the distal end of the scope may be left uncovered to avoid interruption of diagnostic and therapeutic devices or gases delivered via the bronchoscope e.g. LN2 cryospray delivery and LN2 gas egress According to an embodiment of the invention, the bronchoscopic measurement sheath provides thermal insulation of portions of the scope that are inside the patient's body during procedures such as radio frequency, laser, or cryotherapy to provide protection from thermal injury. The braided construction and mix of monofilament and multifilament fibers provide both thermal insulation and a physical barrier between the smooth surface of the bronchoscope and endothelium. As the braided construction can comprise of any combination of polymeric material, there will also be the insulating contribution provided by the polymer. According to other embodiments, the braid may be made from filaments of other compositions (e.g., polypropylene, nylon, polyester) or the braid may be made from a hybrid of filaments made from PET and other materials.

DESCRIPTION OF THE DRAWINGS

The following figures accompany the Detailed Description of the Invention which describes the methods and results of specific examples of the practice and success of the invention.

FIGS. 8A-8D show an exemplary bronchoscopic measurement sheath having an introducer and bronchoscope locking mechanism, suitable for use with embodiments of the invention;

FIGS. 10A-10E show an exemplary bronchoscope-side portion of the locking mechanism shown in FIG. 8A.

FIGS. 11A-11D show the exemplary introducer of FIG. 8A in more detail.

FIG. 12 depicts an alternative embodiment in which the sheath is deployed over the bronchoscope using a retaining tube.

DETAILED DESCRIPTION OF THE INVENTION

Figure 1A:
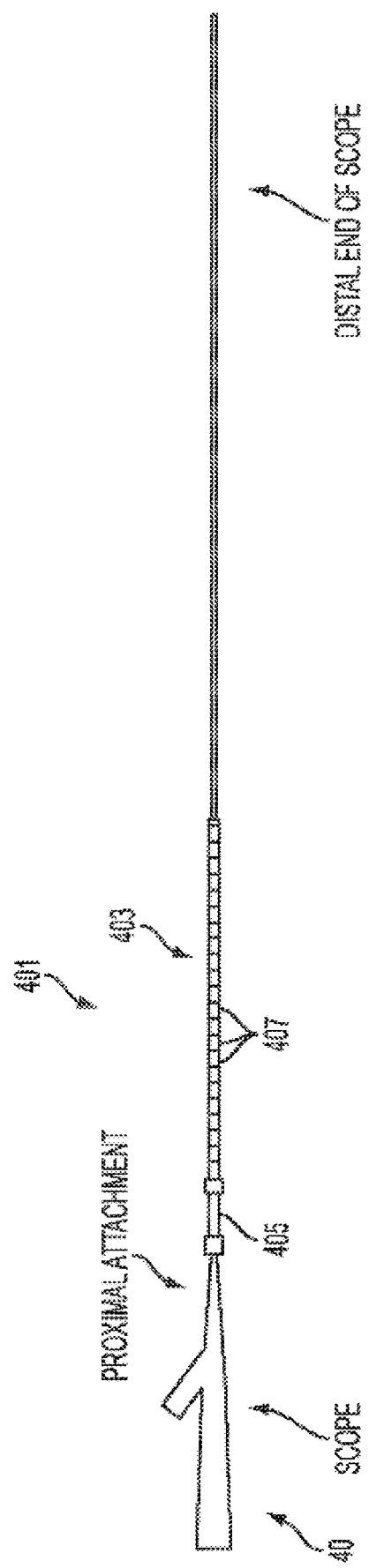
FIGS. 1A-1E depict a bronchoscopic measurement sheath according to an embodiment of the invention, loaded onto the proximal end of a bronchoscope.
Figure 5:
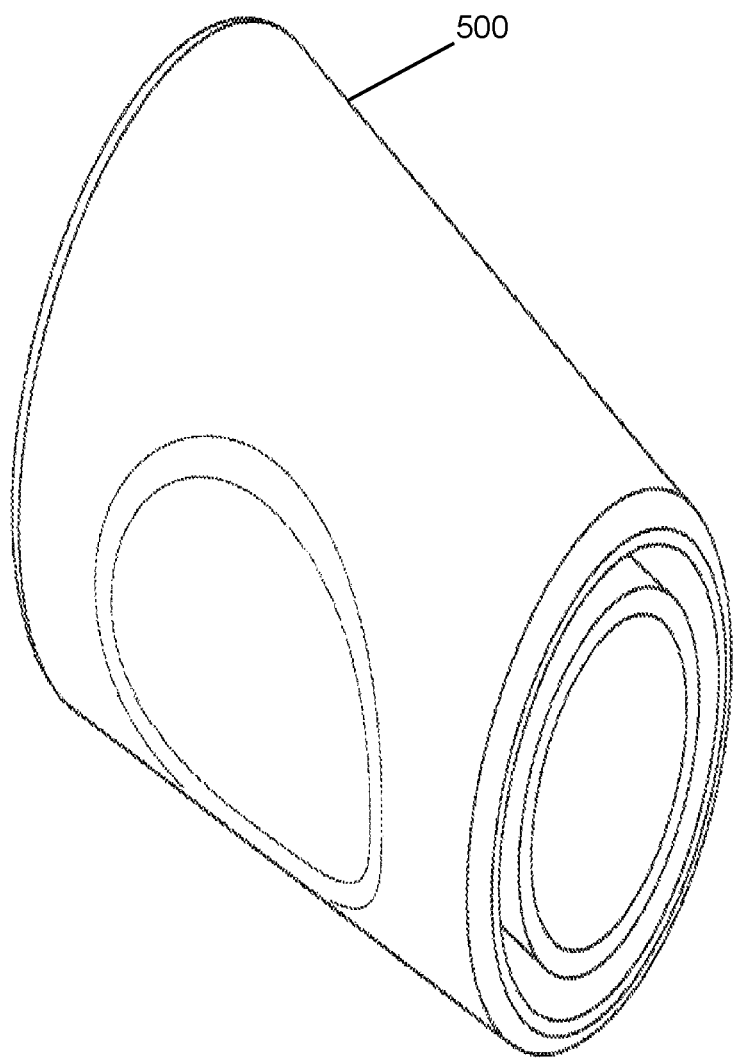
FIG. 5 is a close-up of a bronchoscopic measurement sheath according to another embodiment of the invention, mounted on a flexible fiber-optic bronchoscope.

Referring to FIG. 1A, a bronchoscopic measurement sheath is shown which is configured to be placed over the outer surface of a flexible fiber-optic bronchoscope along a portion of its length during a bronchoscopic procedure. Bronchoscopic measurement sheath 401 may be made of an elongated tube 403 having a lumen configured to receive a bronchoscope 40, a securing device 405, for example a Tuohy-Borst, at one end of said tube configured to secure a proximal end of said sheath to a proximal end of the bronchoscope. According to other embodiment, the securing device is a hub (see, e.g., FIG. 5) fixed to a proximal end of the sheath.

A bronchoscopic measurement sheath may be placed on the outer surface of the flexible bronchoscope to provide reference markings to aid practitioner in measuring movement of the bronchoscope into and out of the patient's airway during diagnostic or therapeutic bronchoscopy A bronchoscopic measurement sheath may be placed on the outer surface of the flexible bronchoscope to aid in discreet placement of doses to prevent overlapping doses when multiple doses are delivered in an anatomical lumen of the same diameter.

Figure 1B:
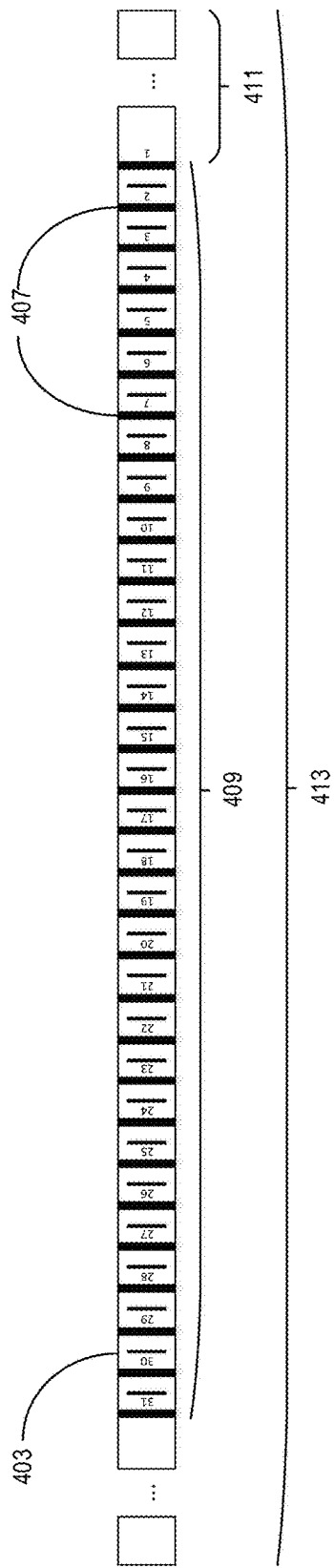
Figure 1C:
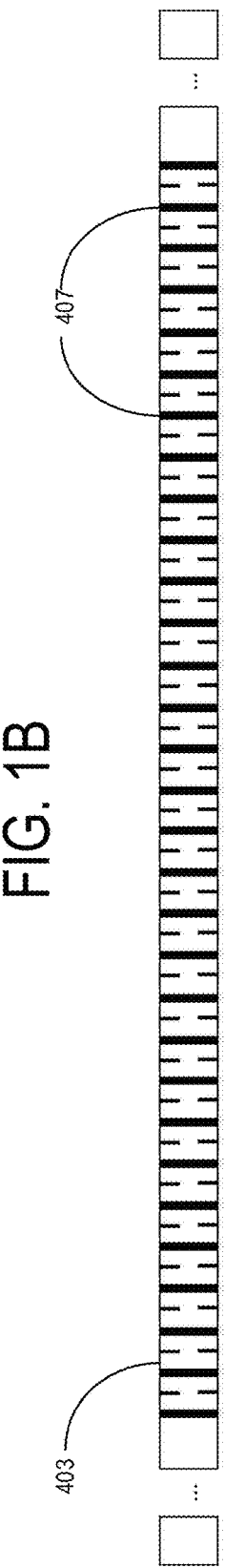

FIGS. 1B-1E depict the sheath as it is manufactured, prior to being cut to an application-specific size. As shown in more detail in FIGS. 1B, 1C, and 1E, the sheath preferably bears a plurality of markings 407 along a portion of the external surface of the tube configured to denote a distance that said scope is moved relative to a fixed position of a patient, a patient feature, or other fixed reference point. FIG. 1B shows the markings 407 from the front side of the sheath, while FIG. 1C shows the markings 407 from the rear side of the sheath.

According to an exemplary embodiment, a distance 409 between the end of the first marking and the end of the final marking is preferably 30 cm (11.81 inches). A distance 411 between the start of the first marking and the end of the tube 403 is preferably 7.9 cm (3.11 inches). An overall length 413 of the tube 403 is preferably 48 cm (18.9 inches). These measurements are taken with respect to the tube 403 when the tube 403 is loaded on a 4.8 mm (+0.1 mm/−0.2 mm) mandrel and allowed to relax, as shown in FIG. 1D. When in an expanded state, the wall thickness of the tube 403 may be about 0.76 mm (about 0.003 inches).

It is noted that, although particular sizes and dimensions are described in connection with exemplary embodiments throughout the application, the present invention is not limited to the described sizes and dimensions. The sizes and dimensions may vary depending on the application.

Figure 1E:
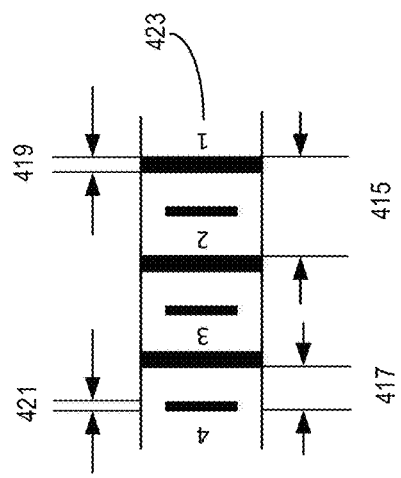
Figure 1D:
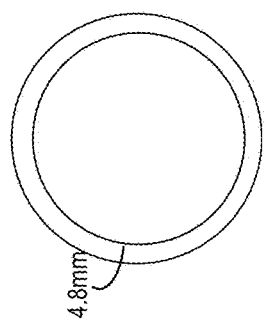

As shown in more detail in FIG. 1E, the markings 407 may include wide markings spaced at a distance 415 of 1 cm apart from each other, and narrower markings spaced at a distance 417 of 0.5 cm from the 1 cm markings. The wide markings may wrap around the circumference of the tube 403 and may have a width 419 of, for example, about 1 mm (+/−0.51 mm). The narrow markings may be broken lines consisting of two bands that have a width 421 of about 0.5 mm and are about 4.3 mm long.

The markings 407 may optionally be associated with printed numbers 423. The numbers 423 may be, for example, about 2 mm tall and written in Arial font, spaced 0.38 mm below each wide 1 cm band.

Accordingly, the markings 407 may be circumferential marker bands outside the working channel of the scope and may optionally be associated with printed numbers. When aligned with a venting tube (e.g. Rigid bronchoscope or endotracheal tube), the markings provide an extracorporeal proximal reference mark prior to dosing. In subsequent doses or treatments, the reference markers assist the physician when the scope is moved to new treatment locations. In the case of dose spacing, the reference markers assist the physician so as not to overlap doses.

Figure 2:
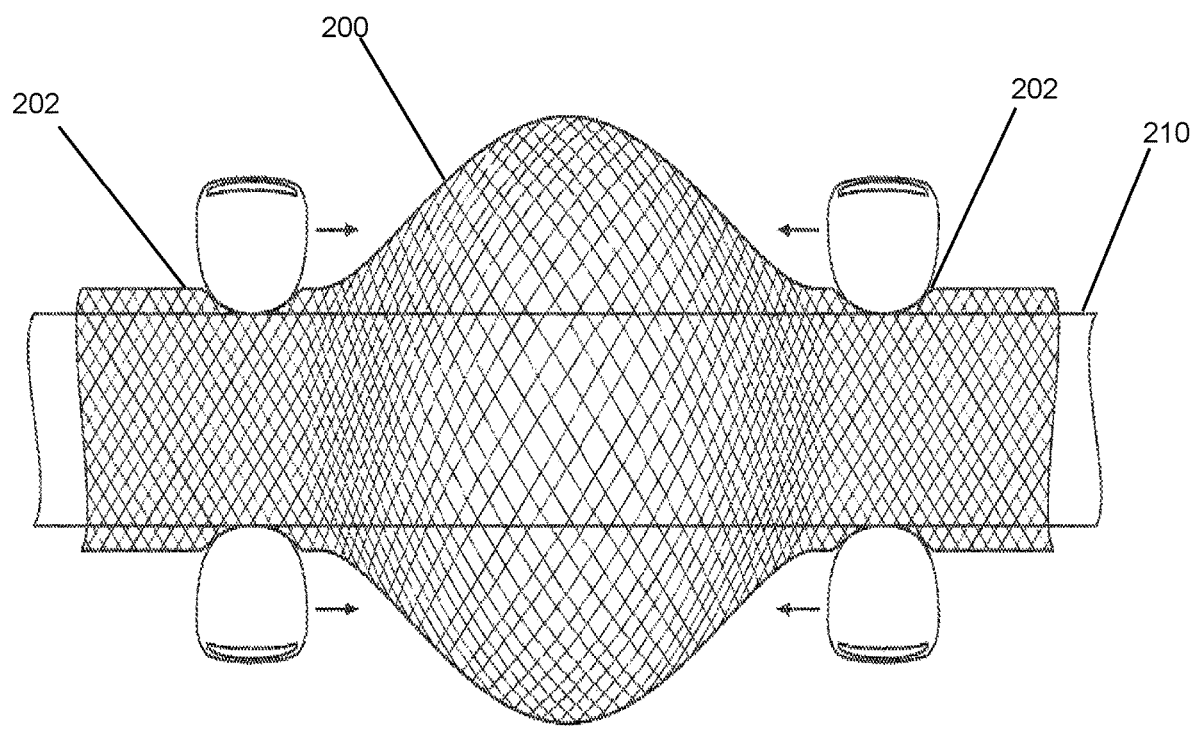
FIG. 2 is a close-up view of a bronchoscopic measurement sheath according to an embodiment of the invention, specifically showing how the sheath expands when the ends are forced together.

FIG. 2 shows how the braid of the sheath 200 is configured to expand and open when the two ends 202 of the sheath 200 are forced together. In order to advance the sheath 200 over the bronchoscope 210 prior to a procedure, or to withdraw the sheath 200 from the bronchoscope 210 after a procedure, the user need only squeeze one end 202 of the sheath 200 tightly against the bronchoscope 210, and advance the other end 202 toward the fixed end 202. When the pinched/fixed end 202 is released, the sheath 200 will relax in that direction. However, when one end 202 of the sheath 200 is pulled, the configuration of the braid causes the sheath 200 to tighten tightly around the bronchoscope 210. Accordingly, the braid of the sheath 200 causes the sheath 200 to work like a Chinese finger puzzle. Accordingly, the sheath 200 will not slide off the bronchoscope 210 as it is being advanced into the endotracheal tube and down a patient's airway. According to a preferred embodiment, the sheath 200 is packaged in a pre-loaded compressed state, so that when it is removed from the packaging for use it is already in the compressed, braid-expanded state which facilitates its application onto the outside surface of the scope 210.

Figure 3:
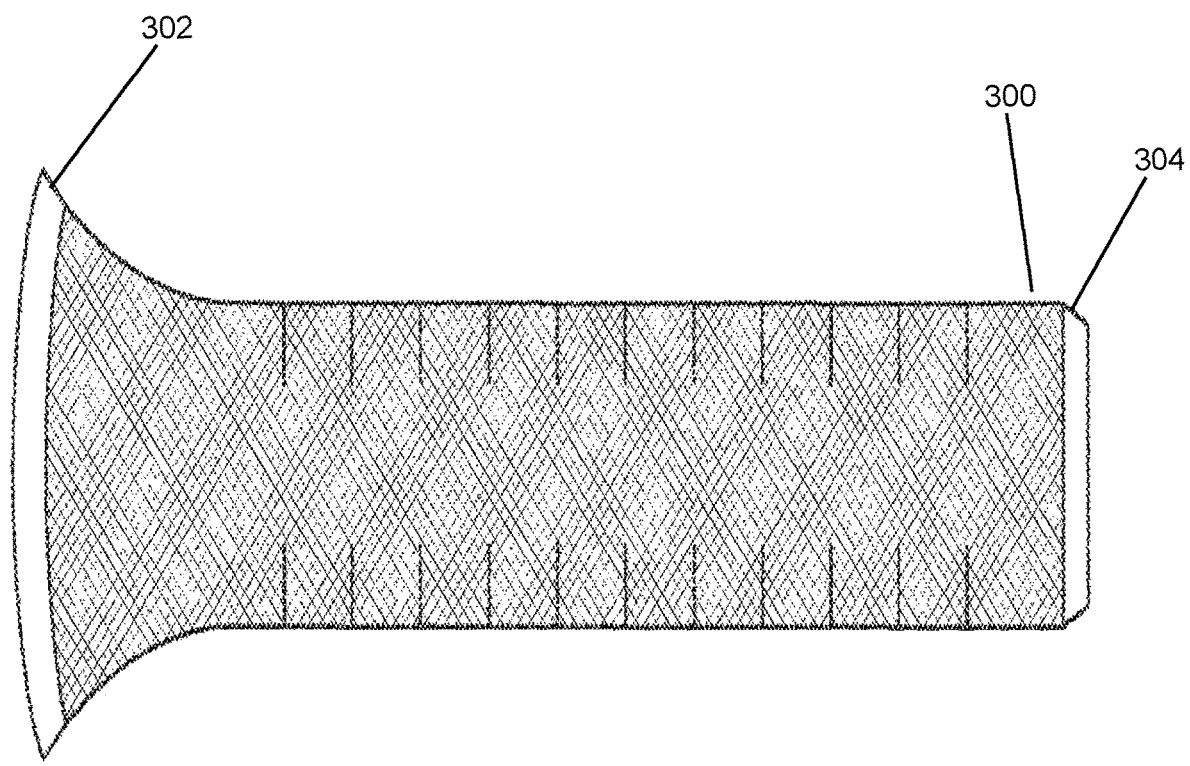
FIG. 3 is a close-up view of a bronchoscopic measurement sheath according to an embodiment of the invention, showing an optional flared proximal end and an optional tapered distal end, with an optional elastomeric cuff at both ends.

FIG. 3 shows a close up of an embodiment of a bronchoscopic measurement sheath 300 according to an embodiment of the invention in which a proximal end 302 of the sheath 300 is cuffed, flared or hubbed and a distal end 304 of the sheath is cuffed and tapered. The optional hub at the proximal end 302 is configured to aid with loading of the sheath 300 onto a bronchoscope, and the optional taper at the distal end 304 is configured to assist with introduction of a sheath-loaded bronchoscope into an endotracheal tube.

According to various embodiments, the sheath may be made of a braided PET (polyethylene terephthalate) polymer monofilament, and the markings are printed on the exterior of the sheath. According to other embodiments, the braid may be made from filaments of other compositions (e.g., polypropylene, nylon, polyester) or the braid may be made from a hybrid of filaments made from PET and other materials. According to a preferred embodiment, the braid is a 72-carrier construction in a 1 over 2 under 2 pattern, the 72 elements comprising 24 elements of 0.0052"PET monofilament at each end, and 48 elements of 85/24 PET multifilament (85 denier/24 filaments). The material may be braided onto a 0.076" acetal substrate core at 38 ppi (pics per inch). According to other embodiments, the braid may be comprised of up to 150 elements of different diameter filaments from 0.004" to 0.01 and up to 50 ppi (pics per inch).

As shown in FIG. 3, either or both ends of the sheath may be formed with a cuff or bonded to prevent or inhibit fraying and/or unraveling of the braid and assist in insertion and removal from the scope.

The end cuffs may be a heat-fused end of the braid itself, or it may be a separate elastomeric (e.g., polyurethane, silicon, etc.) or rigid plastic hub fixed or bonded to the end of the braid. In the case a proximal hub is used, it is preferably shaped to fit the tapered portion of the bronchoscope that connects the working end to the hand piece. According to one embodiment, the hub may be a separate elastomeric element that sandwiches the end of the braid. The hub may be affixed to the braid according to any known methods, including heat bonding, joint bonding, ultra violet light cure, adhesive, or mechanical bonding, such as dipping. According to a preferred embodiment, the hub may be formed with an annular recess (see FIG. 5) configured to receive the heat-sealed edge of the braid. Once the end of the braided tube has been inserted into the annular recess of the hub, adhesive may be dispensed to fill the annular space that receives the braid, bonding the braid into the annular recess. As shown in FIG. 3, the distal end may be tapered for atraumatic insertion in anatomy. According to another embodiment, the distal end may be made have greater stiffness than the remainder of the braid to assist with insertion of the bronchoscope and mounted measurement sheath into the sealing gasket of an endotracheal tube or other laryngeal mask airway, preventing the sheath from buckling and retracting on itself and the bronchoscope as it passes through the tight passage.

Figure 4:
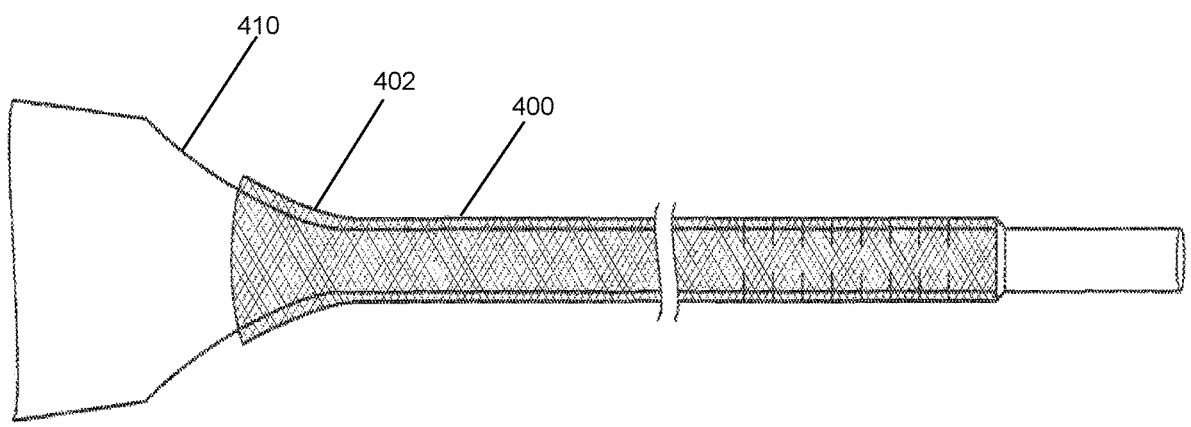

FIG. 4 shows an embodiment of a bronchoscopic measurement sheath 400 mounted on the proximal end of a bronchoscope 410. The proximal portion 402 of the braided sheath may be a heat-fused end of the braid itself, or it may have a separate elastomeric (e.g., polyurethane, silicon, etc.) or rigid plastic element fixed to the end of the braid in order to slide the sheath 400 onto the scope 410 and fix it in place (see, e.g., FIGS. 6 and 7). According to a preferred embodiment, the proximal end 402 has a thermoplastic molded component or "hub" (see, e.g., 500 of FIG. 5) molded onto the braid and having tapered interior profile to accommodate the tapered junction between the proximal end of the flexible fiber optic bronchoscope 410 (the "working portion") and the handpiece.

Figure 6:
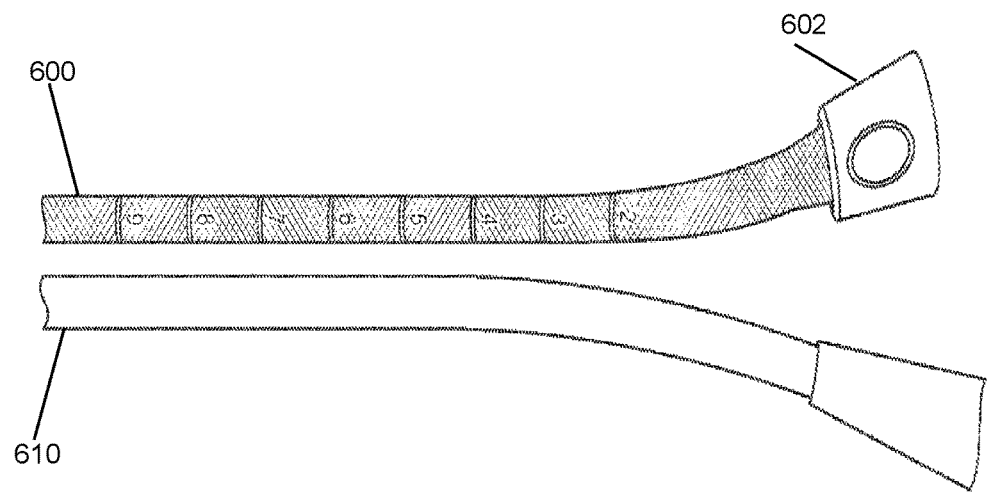
FIG. 6 shows the proximal end of a bronchoscopic measurement sheath according to an embodiment of the invention, next to a flexible bronchoscope.
Figure 7:
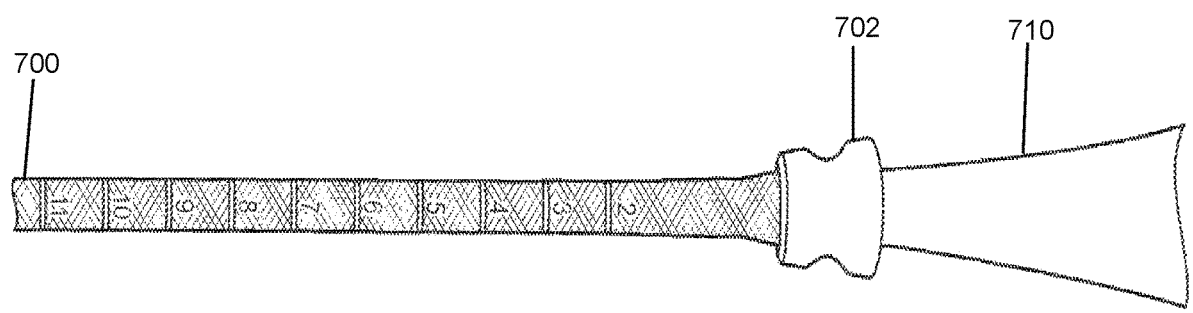
FIG. 7 shows the proximal end of a bronchoscopic measurement sheath according to an embodiment of the invention mounted on the outside of a flexible bronchoscope.

FIG. 6 shows an embodiment of the braided sheath 600 according to the invention, bearing a rigid plastic cuff 602 at the proximal end, next to a flexible bronchoscope 610 onto which it might be loaded. FIG. 7 shows an embodiment of the braided flexible sheath 700 according to the invention loaded onto the outside surface of a flexible bronchoscope 710, with the rigid plastic cuff 702 at the proximal end of the sheath tightly fitted to the tapered portion of the bronchoscope 710 that connects the working end of the bronchoscope 710 to the handpiece of the bronchoscope 710.

Figure 8A:
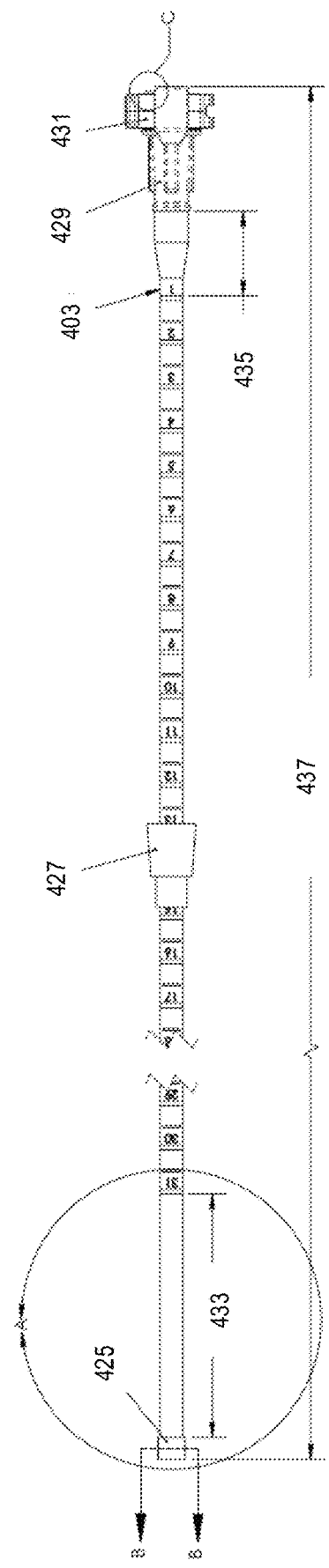

FIG. 8A depicts an exemplary sheath having features for facilitating the insertion of the apparatus into a patient and for securing the apparatus to a bronchoscope.

The sheath includes a distal tip extrusion 425, which is shown in more detail in FIGS. 8B (side view) and 8C (cross-section). The distal tip extrusion 425 shown in FIGS. 8A-8C is cuffed to facilitate insertion of the sheath-mounted bronchoscope into the sealing gasket of the endotracheal tube, to provide an atraumatic end so that the sheath does not scythe the tissue when moving proximal to distal, and/or to prevent fraying and/or unraveling of the braid. The outer diameter of the extrusion 425 may be larger than the inside diameter of the introducer 427, which may help to keep the introducer captive on the assembly. Moreover, the short, stiff section created by the extrusion 425 provides a member for the introducer to push against with the introducer, facilitating insertion of the assembly into the endotracheal tube gasket.

A distance 433 between the end of the distal tip extrusion 425 and the nearest end of the final one of the markings 407 may be about 55 mm (2.17 inches). The outer diameter of the distal tip extrusion 425 may be about 0.240 inches.

The sheath can be locked to a bronchoscope through a proximal hub 429 disposed at the proximal end of the sheath. The proximal hub 429 is shown in more detail in FIGS. 9A-9C. A distance 435 between the nearest end of the first marking 407 may be between about 14 mm (0.5 inches) and about 24 mm (0.9 inches), and preferably is about 19 mm (0.7 inches).

According to some embodiments, one or both of the introducer 427 and the proximal hub 429 may have features or be otherwise configured so that the introducer 427 and the proximal hub 429 can lock together, as described in more detail below in connection with FIGS. 11E-11H.

A slide lock 431 connects to the proximal hub 429 to secure the sheath to a bronchoscope. As shown in the detail view of FIG. 9C, the proximally-facing side of the slide lock 431 includes a feature 433 for which no corresponding feature is present on the distally-facing side of the slide lock 431. Thus, the feature 433 provides an indication of which side of the slide lock 431 should face outward when the apparatus is assembled. A distance 437 between the end of the distal tip extrusion 425 and the end of the slide lock 431 may be between 389.3 mm (15.33 inches) and 427.4 mm (16.83 inches), and preferably is about 408.35 mm (16.08 inches). The slide lock 431 is shown in more detail in FIGS. 10A-10B.

An introducer 427 serves to prop open a gasket on an endotracheal tube to allow the sheath to be deployed in a patient. The introducer 427 is shown in more detail in FIGS. 11A-11D.

The detailed views of the introducer 427, the proximal hub 429, and the slide lock 431 are now described with reference to FIGS. 9A-11D.

Figure 9A:
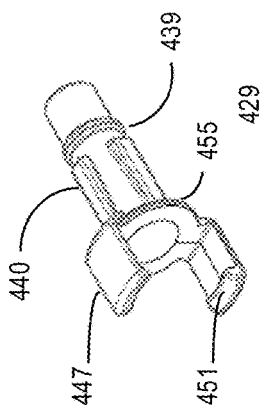
FIGS. 9A-9C show an exemplary sheath-side portion of the locking mechanism shown in FIG. 8A.
Figure 9B:
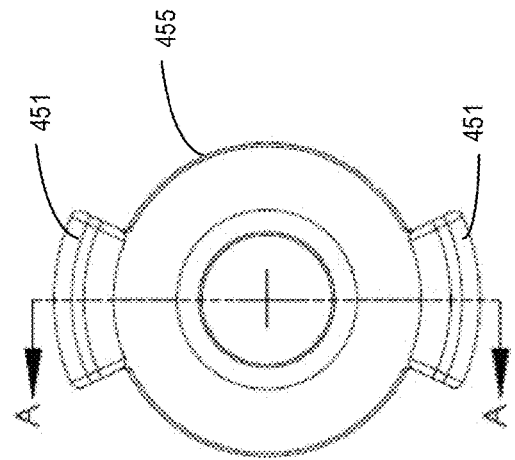
Figure 9C:
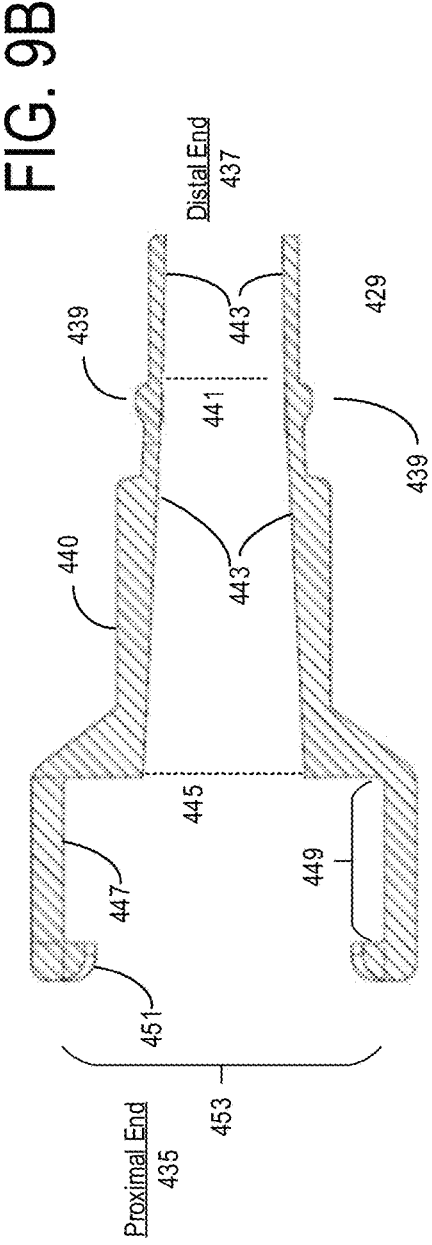

FIG. 9A is a perspective view of the proximal hub 429, whereas FIG. 9B is an end-on view and FIG. 9C is a cross section of the proximal hub 429 taken along the line A-A in FIG. 9B. As shown in FIGS. 9A-9C, the proximal hub 429 includes a proximal end 435 (facing the bronchoscope) and a distal end 437 (which attaches to the sheath). The distal end includes one or more distal features 439 for securing the proximal hub 429 to the sheath. Optionally, the distal end also includes secondary features 440 that provide an indication of a location for securing the introducer 427 to the proximal hub 429. When assembled, the sheath may be pulled up to the distal features 439 and may be bonded to the proximal hub 429 with a bonding agent, such as cyanoacrylate, at the distal outer diameter in the vicinity of the area labeled 443. Alternatively or in addition, the sheath and proximal hub 429 may be insert molded. In one embodiment, the outer diameter at the radially outer end of the distal features 439 is about 0.33 inches, while the outer diameter at the radially outer end of the distal features 440 is about 0.4 inches. This may be compared to an initial radially outer diameter of the proximal hub 429 on the distal side of about 0.28 inches.

The angle of the interior walls changes at a point represented by the broken line 441. On the distal side of the line 441, the walls 443 are angled at about one degree (1°) with respect to a line passing axially through the center of the tube 403 forming the sheath. On the proximal side of the line 441, the walls 445 are angled at about 2.9° from the axial line. As a result, the interior diameter grows from the distal side to the proximal side. For example, in one embodiment, the interior diameter at the line 441 is about 0.230 inches, whereas the interior diameter at a more proximal point 445 is about 0.304 inches. This may be compared to an initial interior diameter on the distal side of 0.22 inches.

Proximal to the point 445, the proximal hub 429 flares outwards into two arms 447. The arms extend a set interior distance 449 from the point 445 before terminating in flanges 451; according to one embodiment, the distance is about 0.310 inches. A distance 453 between the radially interior walls of the arms 447 may be, for example, 0.6 inches. In comparison, an outer radial diameter at the proximal end 435 of the proximal hub 429 may be about 0.72 inches, while a radially outer diameter of a circular support 455 for the arms 447 may be about 0.53 inches.

Figure 10E:
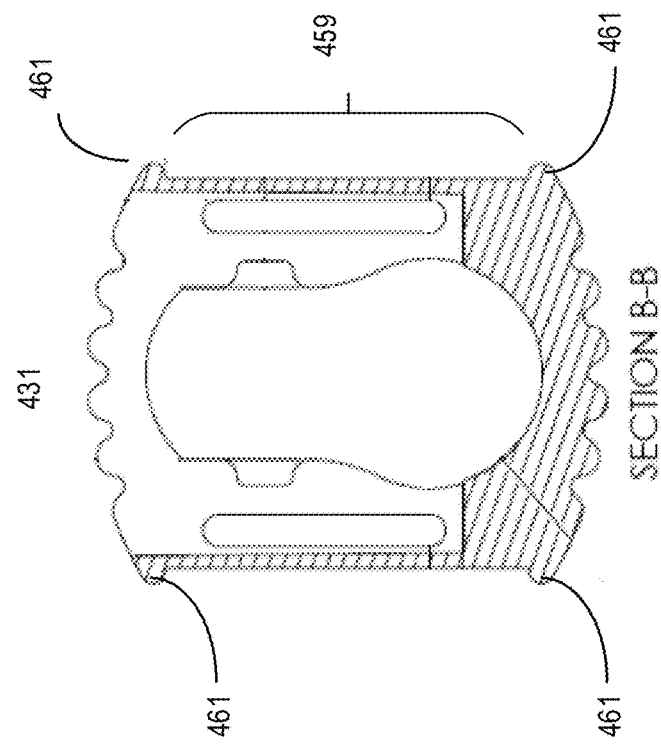
Figure 10D:
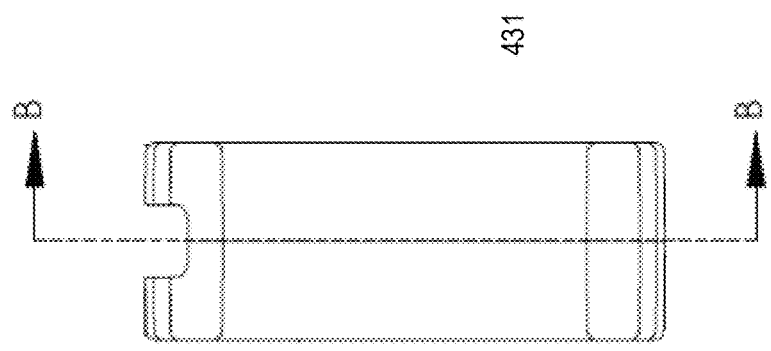

The slide lock 431 is depicted in detail in FIGS. 10A-10E. FIG. 10A is a perspective view of the slide lock 431, while FIG. 10B is an end-on view. FIG. 10C is a cross-section taken at the line A-A in FIG. 10B. FIG. 10D is a side view, and FIG. 10E is a cross-section taken at the line B-B in FIG. 10D.

The slide lock 431 is configured to slot inside of the arms 447 of the proximal hub 429, as shown in FIG. 8A, and to engage with the proximal hub 429 such that the slide lock 431 is secured between the distally-facing interior wall of the flanges 451 and the proximally-facing wall of the circular support 455 for the arms 447 at the point 445. In one embodiment, the slide lock is about 0.30 inches in the width direction 457, 0.8 inches in the height direction 459 as measured at the most radially-exterior points.

The slide lock 431 includes a set of lips 461, and the distance between the lips 461 may be established to facilitate securing the slide lock inside the arms 447 of the proximal hub 429. For example, the distance 463 between the lips 461 may be about 0.550 inches. Excluding the lips 461, the slide lock 431 may have a size of about 0.590 in the length direction 465.

The slide lock 431 includes a central key-shaped hole through which the bronchoscope may pass. The central hole has a central axis 465 extending in the radial direction, and the interior walls of the hole may be angled with respect to the radial direction. The more proximal walls 469 may be angled to a greater degree than the more distal walls 467. For example, the proximal walls 469 may be angled at about 5° with respect to the central axis 465, while the distal walls 467 may be angled at about 0.5° with respect to the central axis 465.

The introducer 427 is depicted in more detail in FIGS. 11A-11D. FIG. 11A is a perspective view of the introducer 427, while FIG. 11B is a side view. FIG. 11C is a cross-section taken at line A-A in FIG. 11B, while FIG. 11D is an end-on view.

The introducer 427 may have a size of about 0.75 inches in the length direction 474. The introducer 427 flares out from a distal end 471 to a proximal end 473. The introducer 427 includes a cylindrical section 475 and a conical section 477. The cylindrical section 475 may be about 0.28 inches long. A radially interior wall 479 of the cylindrical section 475 may have an inner diameter of about 0.22 inches (5.70 mm). The radially interior wall 481 of the conical section 477 may extend at an angle from a central axis passing through the introducer 427 in the axial direction, for example at an angle of about 7°. As a result an inner diameter of the introducer 427 at the proximal end may be about 0.33 inches. At a point where the cylindrical section 475 meets the conical section, the outer diameter of the introducer 427 may grow, for example from 0.28 inches (7 mm) to about 0.37 inches. The outer diameter at the proximal end may be about 0.43 inches.

Figure 11G:
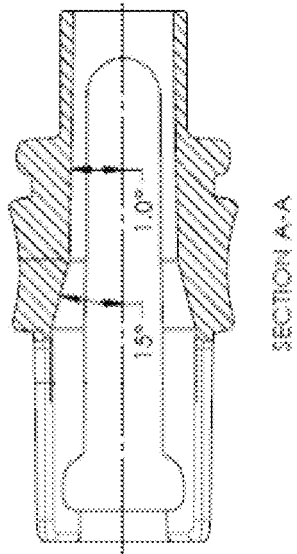
FIGS. 11E-11I depict an alternative example of an introducer.
Figure 11H:
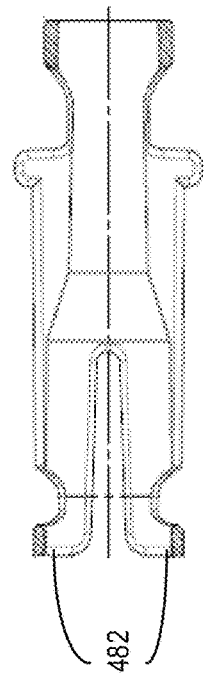
Figure 11E:
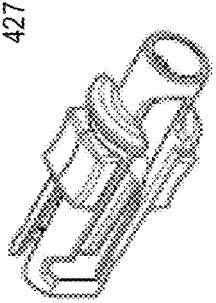
Figure 11F:
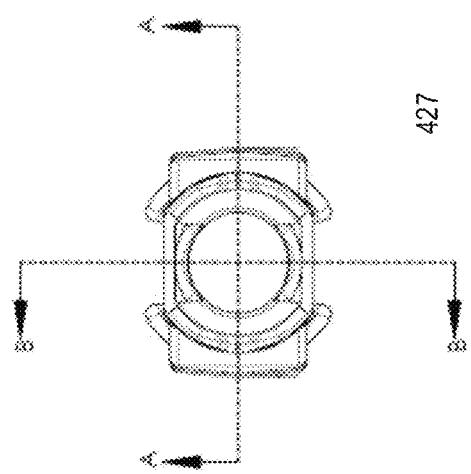
Figure 11I:
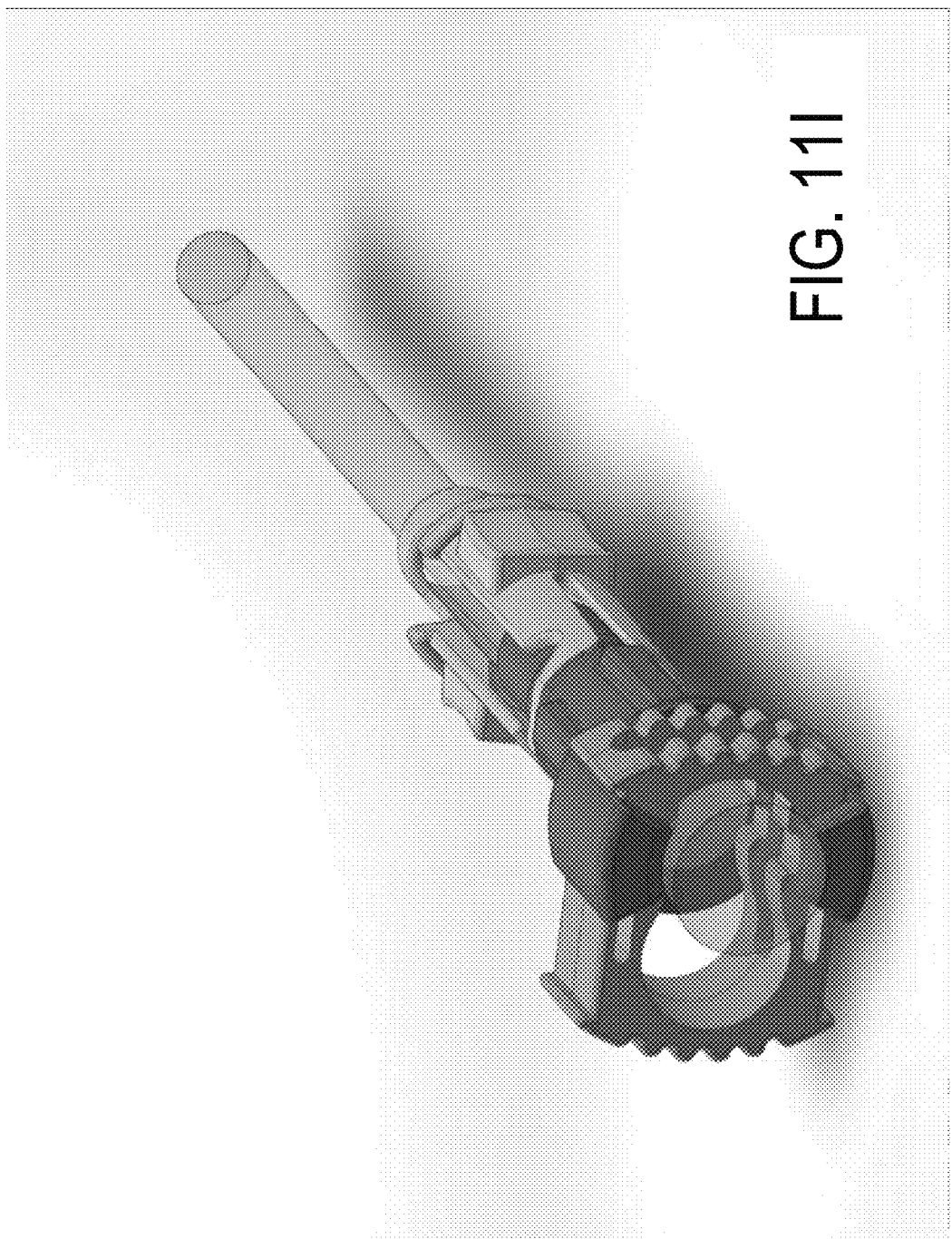

An alternative introducer 427 is shown in FIGS. 11E-11I. This introducer 427 is designed to lock onto the features 439 of the proximal hub 429 to secure the introducer 427 and proximal hub 429 together. When assembled, a set of wings 482 on the introducer 427 are retained between the secondary features 440 of the proximal hub 429 and the features 439 of the proximal hub 440, as shown in FIG. 11I. FIG. 11E is a perspective view of the alternative introducer 427, while FIG. 11G is an end-on view. FIG. 11G is a cross-section taken at line A-A in FIG. 11B, while FIG. 11H is a cross-section taken at line B-B in FIG. 11F. FIG. 11I shows the introducer 427 locked to the proximal hub 429.

As noted above, the sheath 401 may be deployed by "inch-worming" the sheath down the length of the bronchoscope shaft. As an alternative deployment technique (depicted in FIG. 12), a restraining tube 483 may be deployed in connection with the introducer 427. The restraining tube 483 serves to hold the proximal end of the sheath 401 in its compressed (expanded ID) state. The proximal end of the sheath 401 may optionally include a proximal feature designed to be attached to the restraining tube 483 to hold the sheath 401 in place during insertion. The sheath 401 may then be slid onto the scope without the need to inch-worm the sheath 401 up the scope. Once the assembly is deployed on the scope, the restraining tube 483 is removed and the sheath 401 is allowed to extend to its full deployed length.

According to an embodiment of the invention for dose spacing, the invention was initially designed for use in connection with cryospray treatment of a patient's airway using a bronchoscope to allow a user to carefully monitor how far the bronchoscope was being advanced into and/or withdrawn from a patient's airway to ensure that all desired portions of the airway received treatment, but no portion of the airway received more than a single treatment. A flexible bronchoscope is introduced through the nose or mouth as appropriate and the airway is inspected before starting the procedure. The user then navigates the bronchoscope to the targeted site and positions the bronchoscope so that the targeted treatment site is viewed. The dose spacing sheath provides dose spacing guidance when referenced against a fixed reference point such as an endotracheal tube, to allow the bronchoscopist not to dose the same anatomical location more than once.

For example, using the dose spacing sheath to assist with cryospray treatment in Right Lobar Bronchi, the user would navigate sheath-mounted bronchoscope to most distal point of RLL (Right Lower Lobar), noting the marking on the dose spacing sheath relative to a fixed point, e.g. endotracheal tube. The user would then initiate a spray treatment, allow the area to thaw, then withdraw the bronchoscope a discrete distance using the markings on the dose spacing sheath, and then spray a second dose at a second non-overlapping location in the in RLL. The same procedure would be used at any location within the airway to make sure that multiple contiguous or nearly contiguous regions are treated without overlap.

While use of the bronchoscopic measurement sheath and the concept of dose spacing is described herein in the context of cryospray therapy, it can be used for any type of airway treatment in which measure of distance is important.

While use of the bronchoscopic measurement sheath is described herein in the context of airway reference measurement and treatment it can be used for any type of bronchoscopic or endoscopic treatment in which measure of distance is important.

In addition to assisting with dosing, the dose spacing sheath of the invention may be used as a measuring device for any bronchoscopic procedure to document the location of lesions, strictures, treatment sites or length of airway segments.

The invention claimed is:

1. An endoscopic sheath configured to be placed over an outer surface of an endoscope along a portion of a length of said endoscope during an endoscopic procedure, comprising:
    an elongated tube having a lumen configured to receive said endoscope;
    a securing device at one end of said elongated tube configured to secure said endoscopic sheath to a proximal portion of said endoscope; and
    a plurality of markings along a portion of an external surface of said elongated tube configured to denote a distance that said endoscope is moved relative to a fixed reference point;
    wherein said elongated tube comprises a braid, the braid having a distal end configured to mount to said outer surface of said endoscope such that said distal end is configured to tighten about said endoscope when the braid is pulled proximally, and wherein the braid changes diameter when ends of said elongated tube are moved toward and away from one-another.

2. The endoscopic sheath according to claim 1, wherein said plurality of markings are circumferential marker bands.

3. The endoscopic sheath according to claim 1, wherein said plurality of markings are outside a working channel of said endoscope.

4. The endoscopic sheath according to claim 1 wherein said plurality of markings are associated with printed numbers.

5. The endoscopic sheath according to claim 1, wherein said elongated tube comprises braided monofilaments, is configured to collapse and tighten under tension, and open and expand when ends of said elongated tube are pushed toward one-another.

6. The endoscopic sheath according to claim 1, wherein a proximal end of said elongated tube is flared.

7. The endoscopic sheath according to claim 1, wherein a distal end of said elongated tube is tapered.

8. The endoscopic sheath according to claim 1, further comprising a cuff fixed to an end of said elongated tube.

9. The endoscopic sheath according to claim 8, wherein each end of said elongated tube has a cuff.

10. The endoscopic sheath according to claim 1, wherein said plurality of markings provide dose spacing reference points for a user performing multiple doses in one procedure.

11. The endoscopic sheath according to claim 1, configured to provide thermal insulation properties for said endoscope.

12. The endoscopic sheath according to claim 1, comprising a distal end of said elongated tube that is stiffer than other portions of said endoscopic sheath in order to facilitate insertion of said endoscope and said endoscopic sheath placed thereover without causing said endoscopic sheath to retract on said endoscope.

13. The endoscopic sheath according to claim 1, comprising a tapered distal end to facilitate insertion of said endoscope and said endoscopic sheath placed thereover through tight openings without causing said endoscopic sheath to retract on said endoscope.

14. The endoscopic sheath according to claim 1, further comprising a hub affixed to a proximal end of said endoscopic sheath and configured to mount on a tapered portion of said endoscope between a working end and a handpiece of said endoscope.

15. The endoscopic sheath according to claim 14, wherein said hub is tapered and wherein a distal end of said hub defines an annular recess for receiving a proximal end of said sheath.

16. The endoscopic sheath according to claim 14, wherein said hub is configured to lock onto an introducer configured to facilitate insertion of said endoscopic sheath and said endoscope into an endotracheal tube.

17. The endoscopic sheath according to claim 14, further comprising a slide lock for locking said sheath to said endoscope.

18. The endoscopic sheath according to claim 17, wherein said slide lock is configured to lock to said hub.

19. An apparatus comprising said endoscopic sheath according to claim 1, further comprising a restraining tube configured to hold said endoscopic sheath in an open and expanded state during deployment of said endoscopic sheath.

20. The endoscopic sheath according to claim 1, wherein the distal end of the braid is slidably mounted to the outer surface of said endoscope.

* * * * *